(12) United States Patent
Petz

(10) Patent No.: US 12,048,825 B2
(45) Date of Patent: Jul. 30, 2024

(54) ROTARY TATTOO MACHINES WITH IMPROVED ADJUSTABILITY

(71) Applicant: James Nathan Petz, Gresham, OR (US)

(72) Inventor: James Nathan Petz, Gresham, OR (US)

( * ) Notice: Subject to any disclaimer, the term of this patent is extended or adjusted under 35 U.S.C. 154(b) by 596 days.

(21) Appl. No.: 17/336,671

(22) Filed: Jun. 2, 2021

(65) Prior Publication Data

US 2022/0387773 A1    Dec. 8, 2022

(51) Int. Cl.
*A61M 37/00* (2006.01)
(52) U.S. Cl.
CPC .............................. *A61M 37/0076* (2013.01)
(58) Field of Classification Search
CPC .......................... A61M 37/00; A61M 31/0076
USPC ......................................................... 81/9.22
See application file for complete search history.

(56) References Cited

U.S. PATENT DOCUMENTS

2016/0263365 A1* 9/2016 Smith ............... A61M 37/0076

* cited by examiner

*Primary Examiner* — Tom Rodgers
(74) *Attorney, Agent, or Firm* — Mohr Intellectual Property Law Solutions

(57) ABSTRACT

Tattoo machines configured to drive a needle towards a marking area. The tattoo machines include a motor, a first arm, a second arm, and a primary spring. The first arm is operatively connected to the motor and driven by the motor towards the marking area. The second arm is spaced from the first arm and configured to couple to the needle. The primary spring is biased to move the first arm and the second arm away from the marking area. The second arm is driven towards the marking area when the first arm is driven towards the marking area by the motor.

17 Claims, 8 Drawing Sheets

ROTARY TATTOO MACHINES WITH IMPROVED ADJUSTABILITY

BACKGROUND

The present disclosure relates generally to tattoo machines. In particular, rotary tattoo machines with improved adjustability are described.

Tattoos are a popular form of body embellishment. A tattoo is a permanent marking of the skin with indelible ink.

A tattoo machine is a hand-held device used to create a tattoo on a person's skin. Modern tattoo machines use electromagnetic coils to move an armature bar up and down. These machines are often called coil tattoo machines. Coil tattoo machines include an armature bar that moves in response to an electromagnetic current. Connected to the armature bar is a needle grouping that pushes ink into the skin.

In addition to coil tattoo machines, there are also rotary tattoo machines. Rotary tattoo machines are powered by regulated motors rather than electromagnetic coils.

Known tattoo machines are not entirely satisfactory for the range of applications in which they are employed. For example, existing coil tattoo machines get hot and make a lot of noise, which makes them unpleasant to use for extended periods. Rotary machines tend to have limited adjustability, which can make them less effective at creating detailed tattoos.

Thus, there exists a need for tattoo machines that improve upon and advance the design of known tattoo machines. Examples of new and useful tattoo machines relevant to the needs existing in the field are discussed below.

SUMMARY

The present disclosure is directed to tattoo machines configured to drive a needle towards a marking area. The tattoo machines include a motor, a first arm, a second arm, and a primary spring. The first arm is operatively connected to the motor and driven by the motor towards the marking area. The second arm is spaced from the first arm and configured to couple to the needle. The primary spring is biased to move the first arm and the second arm away from the marking area. The second arm is driven towards the marking area when the first arm is driven towards the marking area by the motor.

DETAILED DESCRIPTION

Figure 1:
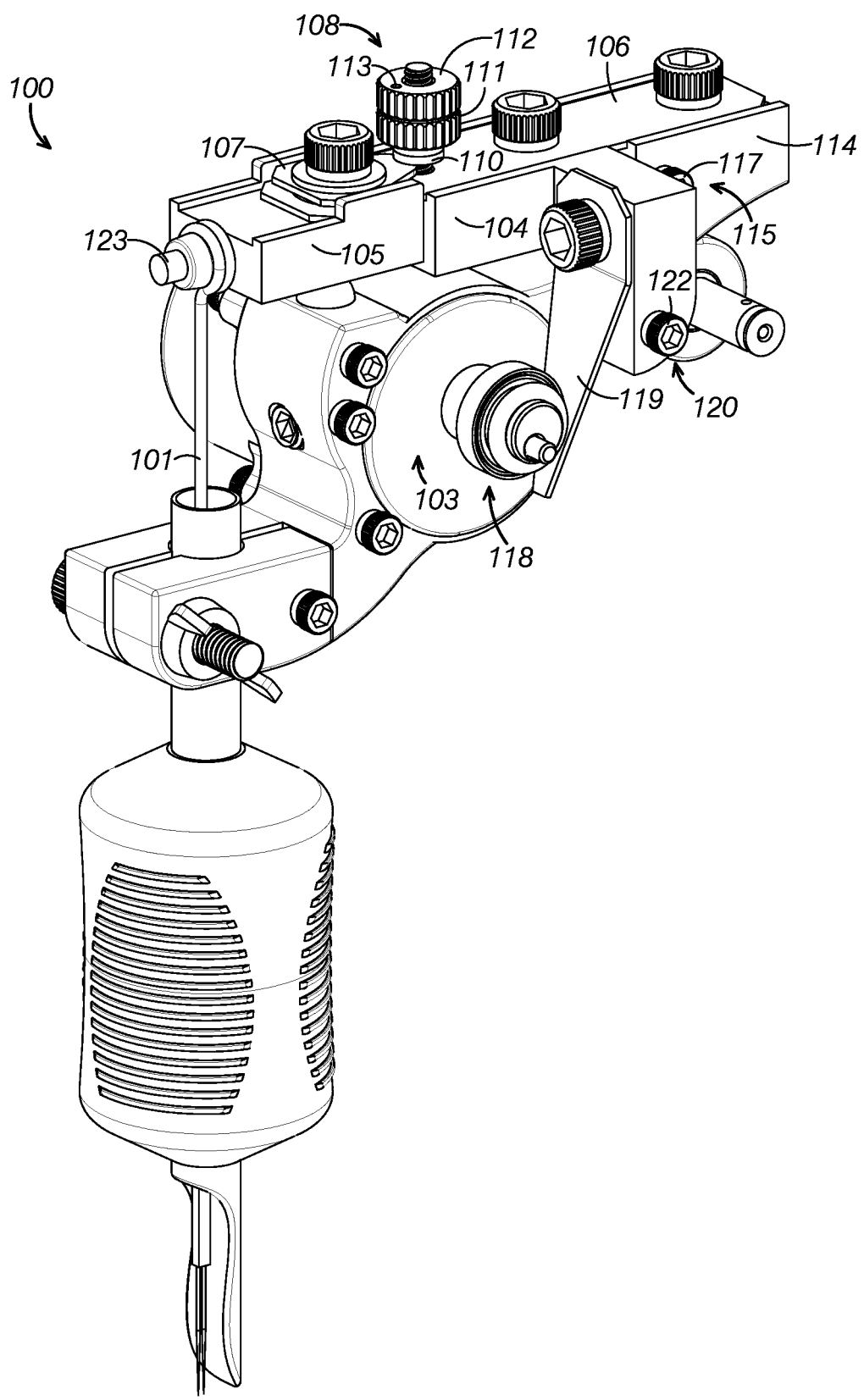
FIG. 1 is a front, left perspective view of a first embodiment of a tattoo machine.

The disclosed tattoo machines will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various tattoo machines are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components.

"Communicatively coupled" means that an electronic device exchanges information with another electronic device, either wirelessly or with a wire-based connector, whether directly or indirectly through a communication network.

"Controllably coupled" means that an electronic device controls operation of another electronic device.

Rotary Tattoo Machines with Improved Adjustability

With reference to the figures, rotary tattoo machines with improved adjustability will now be described. The tattoo machines discussed herein function to create a tattoo on a person's skin.

The reader will appreciate from the figures and description below that the presently disclosed tattoo machines address many of the shortcomings of conventional tattoo machines. For example, the tattoo machines described below avoid the excessive heat and noise of conventional coil tattoo machines. As a result, the tattoo machines disclosed in this application are considerably more pleasant to use for extended periods than existing coil tattoo machines.

The tattoo machines discussed herein utilize rotary motors. However, the newly invented rotary tattoo machines described below have more adjustability than conventional rotary tattoo machines. A benefit of the increased adjustability of the tattoo machines below is that they are more effective at creating detailed tattoos than conventional rotary tattoo machines.

Contextual Details

Ancillary features relevant to the tattoo machines described herein will first be described to provide context and to aid the discussion of the tattoo machines.

Needle

Tattoo needles are used with the tattoo machines described below to transfer ink into a person's skin. As shown in FIGS. 1-5, a needle 101 couples to tattoo machine 100 and is driven up and down by tattoo machine 100. In particular, the reader can see in FIGS. 1-5 that needle 101 couples to a post 123 of a second arm 105 of tattoo machine 100.

The needle may be any currently known or later developed type of tattoo needle. The reader will appreciate that a variety of needle types exist and could be used in place of the needle shown in the figures. In addition to the types of needles existing currently, it is contemplated that the tattoo machines described herein could incorporate new types of needles developed in the future.

The size of the needle may be varied as needed for a given application. In some examples, the needle is larger relative to the other components than depicted in the figures. In other examples, the needle is smaller relative to the other components than depicted in the figures. Further, the reader should understand that the needle and the other components may all be larger or smaller than described herein while maintaining their relative proportions.

Tattoo Machine Embodiment One

With reference to FIGS. 1-8, a tattoo machine 100 will now be described as a first example of a tattoo machine. As depicted in FIG. 1, tattoo machine 100 is configured to drive a needle 101 towards a tattoo marking area on a person's body. The reader can see in FIGS. 1-8 that tattoo machine 100 includes a motor 103, a first arm 104, a second arm 105, a primary spring 106, a secondary spring 107, a fine adjustment device 108, an anchor member 114, a primary spring adjustment device 115, an input spring 119, and an input adjustment device 120. In other examples, the tattoo machine includes fewer components than depicted in the figures. In certain examples, the tattoo machine includes additional or alternative components than depicted in the figures.

Motor

Motor 103 functions to drive components of tattoo machine 100 to ultimately drive needle 101 towards the tattoo marking area. As depicted in FIGS. 1, 3, and 5-8, motor 103 includes an output shaft 118. Output shaft 118 contacts input spring 119 once per rotation to act on input spring 119 cyclically.

The drive train will be described in this paragraph to explain how motor 103 acts on other components of tattoo machine 100. As shown in FIGS. 1-8, motor 103 rotates an output shaft 118, which drives an input spring 119. Input spring 119 pulls on first arm 104 and primary spring 106 coupled to first arm 104. Primary spring 106 then moves second arm 105 supporting needle 101 towards the tattoo marking area. Secondary spring 107 modifies how second arm 105 moves towards the tattoo marking area in response to primary spring 106.

The reader can understand from the mechanical arrangement depicted in FIGS. 1-7 that adjusting the speed of motor 103 controls, in part, how second arm 105 moves towards the tattoo marking area. Second arm 105 moves towards the target marking area in response to first arm 104 and primary spring 106 moving towards the marking area ultimately from the urging of motor 103.

The motor may be any currently known or later developed type of motor. The reader will appreciate that a variety of motor types exist and could be used in place of the motor shown in the figures. In addition to the types of motors existing currently, it is contemplated that the tattoo machines described herein could incorporate new types of motors developed in the future.

The size of the motor may be varied as needed for a given application. In some examples, the motor is larger relative to the other components than depicted in the figures. In other examples, the motor is smaller relative to the other components than depicted in the figures. Further, the reader should understand that the motor and the other components may all be larger or smaller than described herein while maintaining their relative proportions.

Input Spring

Input spring 119 functions to transfer motion from output shaft 118 of motor 103 to first arm 104. Input spring 119 pulls first arm 104 towards the tattoo marking area when output shaft 118 presses on input spring 119. As shown in FIGS. 1, 3, 5, and 6, input spring 119 is coupled to first arm 104 and driven by output shaft 118.

The size of the input spring may be varied as needed for a given application. In some examples, the input spring is larger relative to the other components than depicted in the figures. In other examples, the input spring is smaller relative to the other components than depicted in the figures. Further, the reader should understand that the input spring and the other components may all be larger or smaller than described herein while maintaining their relative proportions.

Input Adjustment Device

With reference to FIGS. 1, 3, and 5-8, input adjustment device 120 is configured to adjust the position of input spring 119 relative to output shaft 118 of motor 103. As shown in FIGS. 1, 3, and 5-8, input adjustment device 120 includes an input adjustment screw 121 and an input set screw 122. The reader can see in FIG. 8 that input adjustment screw 121 selectively abuts input spring 119. As depicted in FIGS. 1, 3, and 5-7, input set screw 122 selectively fixes the position of input adjustment screw 121 by selectively abutting input adjustment screw 121 with user-selected compressive force.

Anchor Member

Anchor member 114 functions to support primary spring 106 and other components of tattoo machine 100. With reference to FIGS. 1-4 and 6-8, the reader can see that anchor member 114 is disposed proximate first arm 104 opposite second arm 105.

Arms

The arms serve to move needle 101 towards the tattoo marking area. The arms further serve to support other components of tattoo marking machine 100, such as input spring 119 and fine adjustment device 108.

Figure 2:
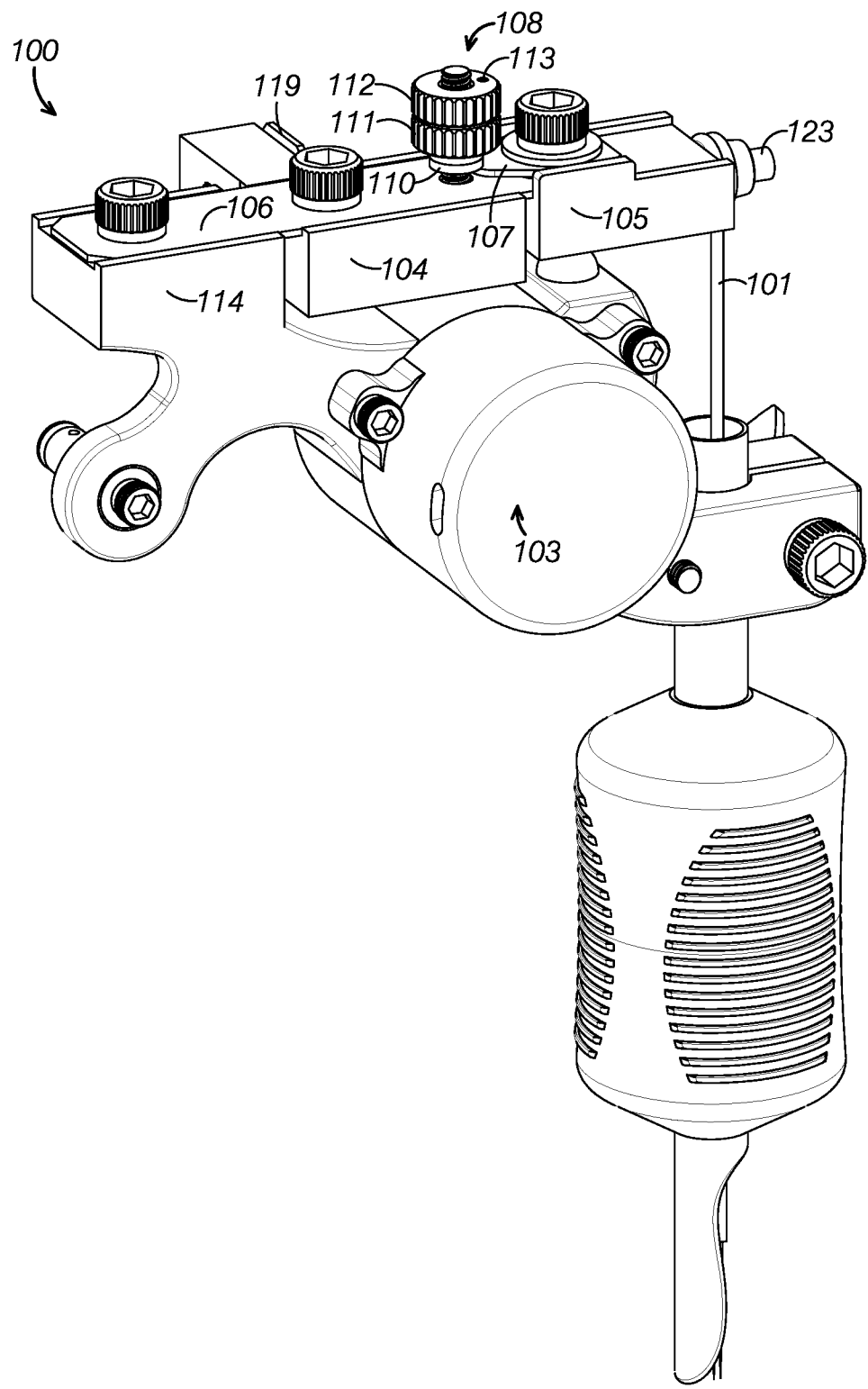
FIG. 2 is a rear, right perspective view of the tattoo machine shown in FIG. 1.
Figure 3:
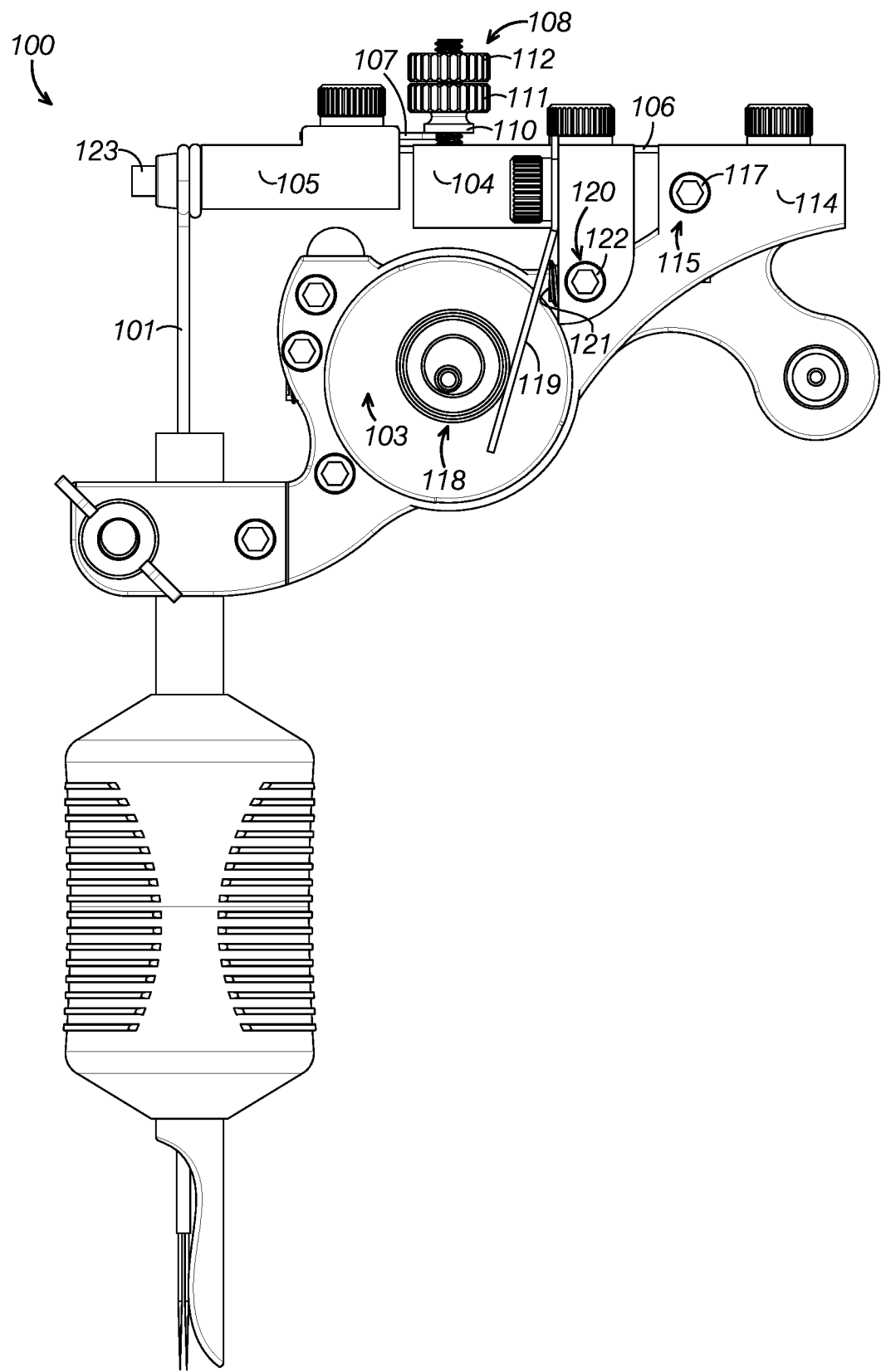
FIG. 3 is a left side elevation view of the tattoo machine depicted in FIG. 1.
Figure 4:
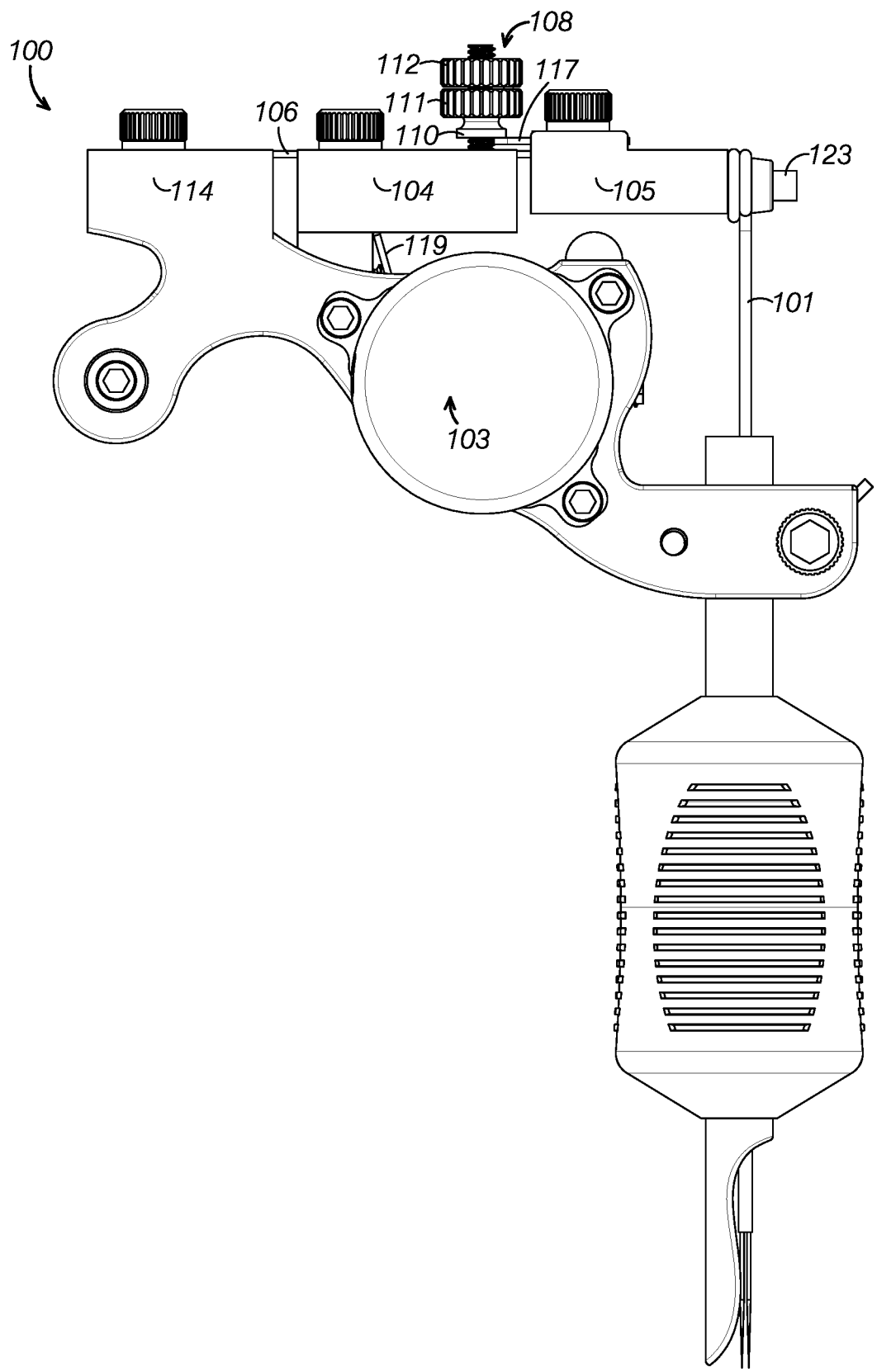
FIG. 4 is a right side elevation view of the tattoo machine depicted in FIG. 1.
Figure 5:
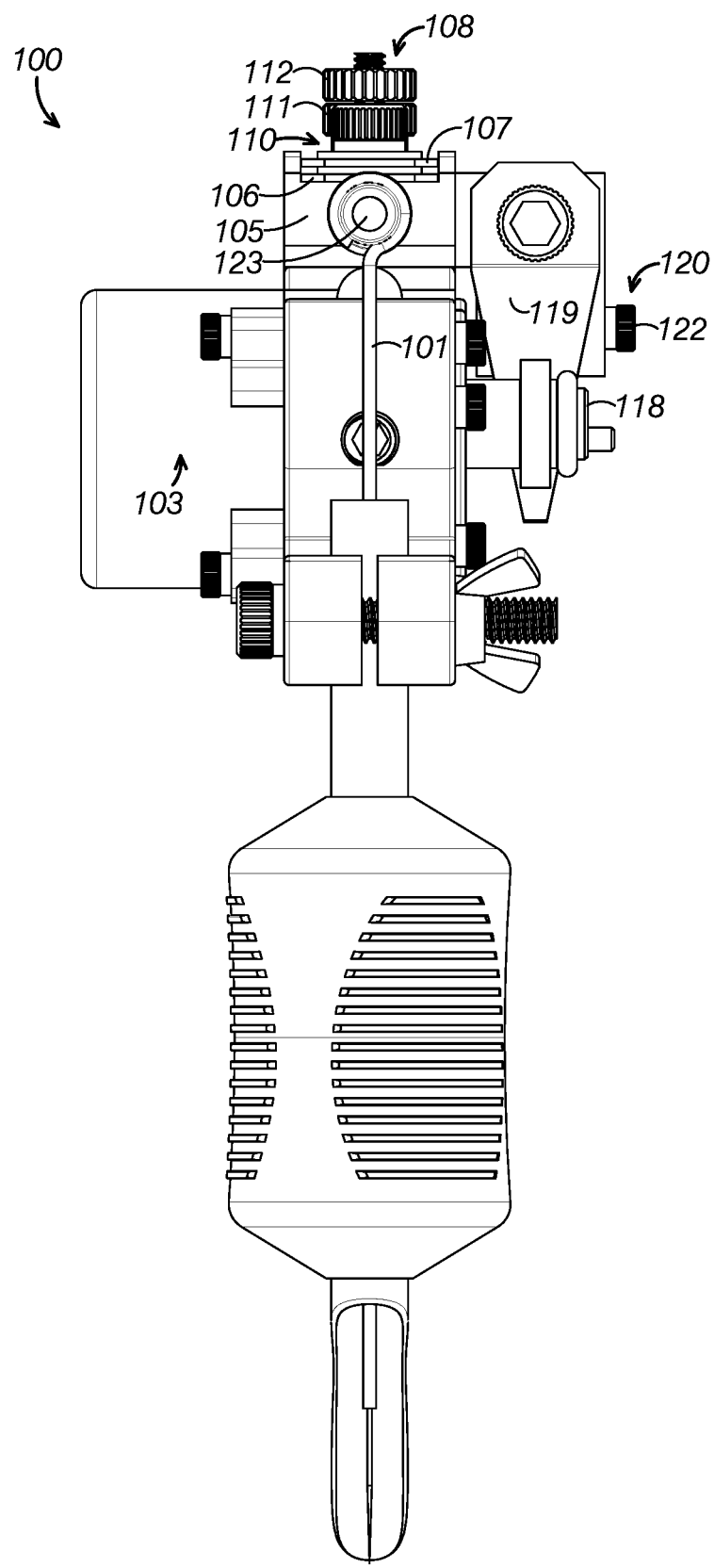
FIG. 5 is a front elevation view of the tattoo machine depicted in FIG. 1.

In the example shown in FIGS. 1-8, tattoo machine includes two arms: first arm 104 and second arm 105. With reference to FIGS. 1, 3, and 5, first arm 104 is operatively connected to motor 103 by input spring 119. First arm 104 is driven towards marking area 102 by motor 103 acting on input spring 119.

Figure 7:
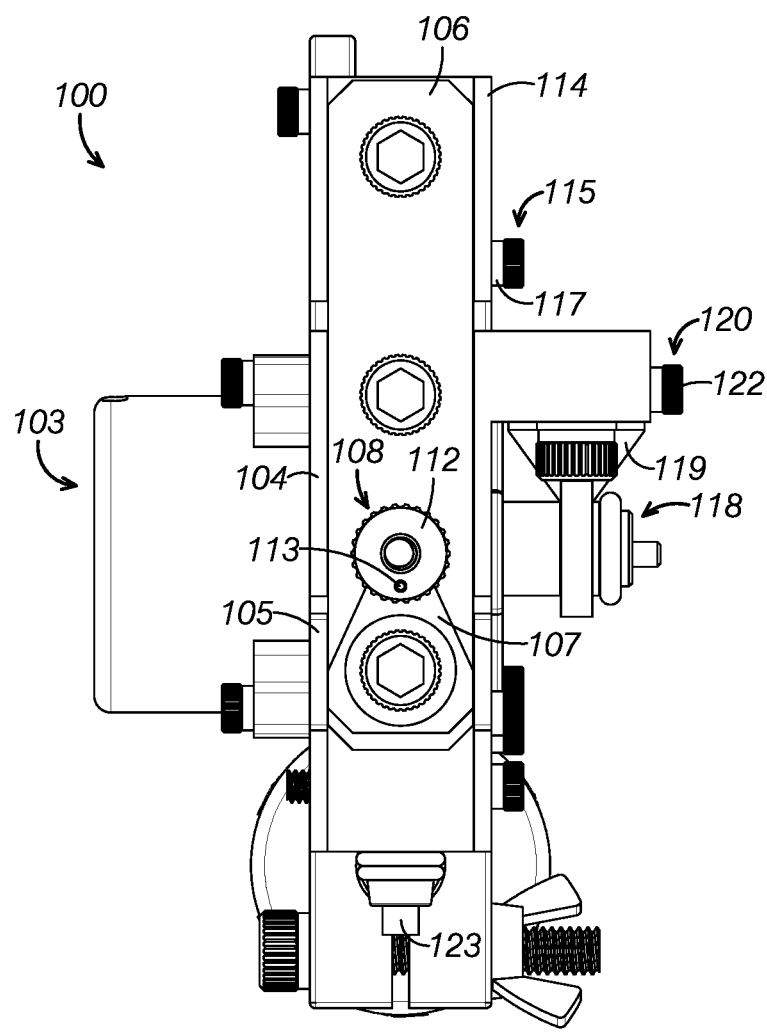
FIG. 7 is a top view of the tattoo machine depicted in FIG. 1

The reader can see in FIGS. 1-4 and 7 that second arm 105 spaced from first arm 104 and linked to first arm 104 by primary spring 106 and secondary spring 107. As depicted in FIGS. 1-5 and 7, second arm 105 includes a post 123 opposite first arm 104. Second arm 105 supports needle 101 on post 123. As shown in FIGS. 1, 2, and 7, second arm 105 is driven towards the marking area when first arm 104 is driven towards the marking area by motor 103.

The size of the arms may be varied as needed for a given application. In some examples, the arms are larger relative to the other components than depicted in the figures. In other examples, the arms are smaller relative to the other components than depicted in the figures. Further, the reader should understand that the arms and the other components may all be larger or smaller than described herein while maintaining their relative proportions.

In the present example, the arms are comprised of metal. However, the arms may be comprised of any currently known or later developed material suitable for their functions in the tattoo machine. Suitable materials include metals, polymers, wood, ceramics, and composite materials.

Primary Spring

The role of primary spring 106 is to link and move first arm 104 and second arm 105. With reference to FIGS. 1, 2, and 7, primary spring 106 is biased to move first arm 104 and second arm 105 away from marking area 102 after they are driven towards the marking area by motor 103. Further, as the reader can understand from the mechanical arrangement depicted in FIGS. 1-7, primary spring 106 and secondary spring 107 resiliently whip second arm 105 towards the marking area when first arm 104 moves towards the marking area.

As shown in FIGS. 1, 2, and 7, primary spring 106 is substantially planer. As depicted in FIGS. 1, 2, and 7, primary spring 106 is coupled to anchor member 114.

The size of the primary spring may be varied as needed for a given application. In some examples, the primary spring is larger relative to the other components than depicted in the figures. In other examples, the primary spring is smaller relative to the other components than depicted in the figures. Further, the reader should understand that the primary spring and the other components may all be larger or smaller than described herein while maintaining their relative proportions.

Primary Spring Adjustment Device

Primary spring adjustment device 115 functions to adjust the flex of primary spring 106. As shown in FIGS. 1-4, 6, and 7, primary spring adjustment device 115 is coupled to anchor member 114. The reader can see in FIGS. 1-4, 6, and 7 that primary spring adjustment device 115 includes a primary spring adjustment screw 116 and a primary spring set screw 117.

Figure 6:
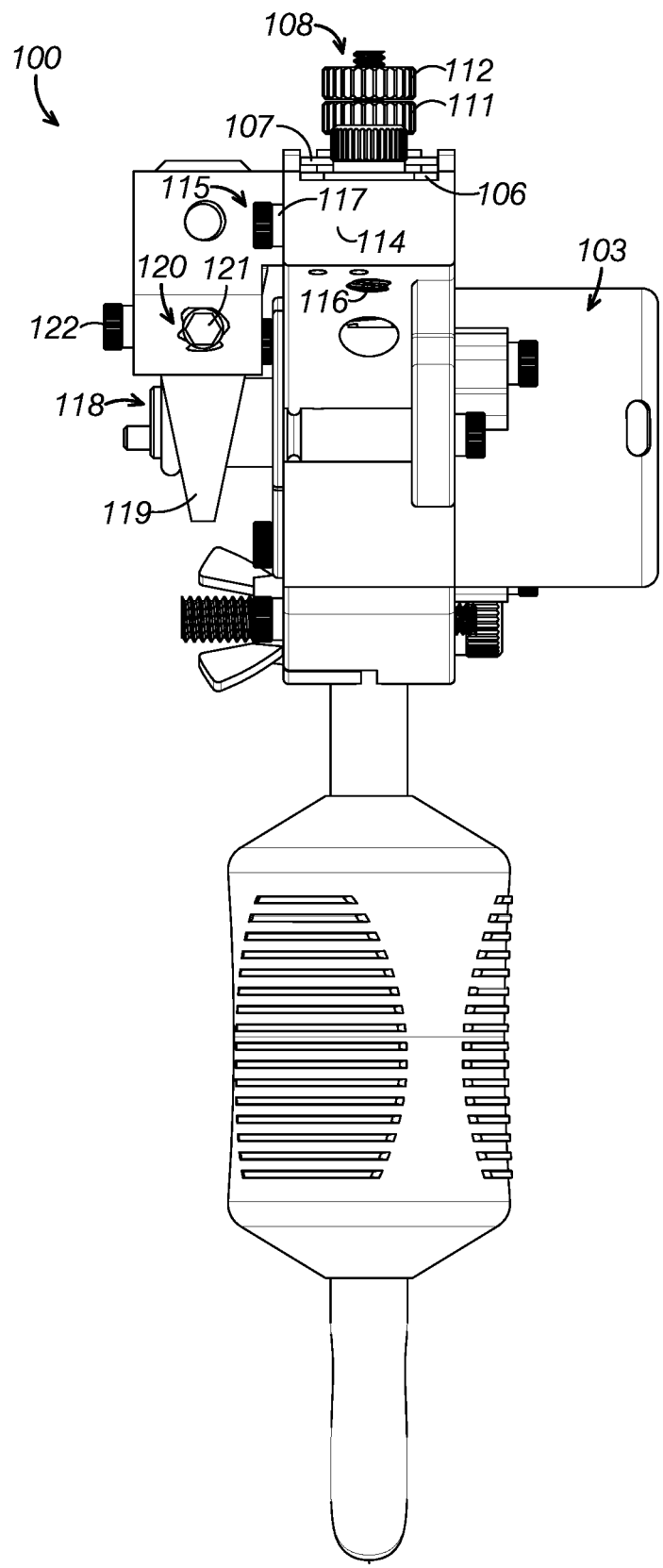
FIG. 6 is a rear elevation view of the tattoo machine depicted in FIG. 1.
Figure 8:
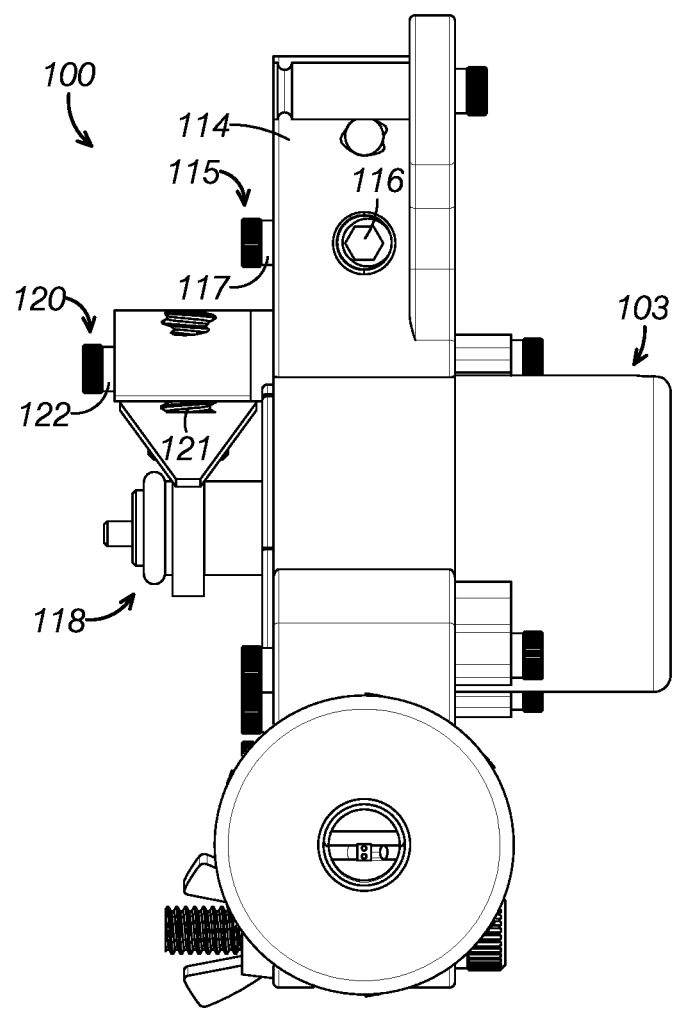
FIG. 8 is a bottom view of the tattoo machine depicted in FIG. 1

As depicted in FIGS. 6 and 8, primary spring adjustment screw 116 selectively abuts primary spring 106 and exerts compressive force on primary spring 106. By modifying the compressive force exerted on primary spring 106, primary spring adjustment screw 116 adjusts the flex of primary spring 106.

The role of primary spring set screw 117 is to selectively fix the position of primary spring adjustment screw 116. Primary spring set screw 117 selectively abuts primary spring adjustment screw 116 with user-selected compressive force to fix the position of primary spring adjustment screw 116.

Secondary Spring

Secondary spring 107 functions to modify how second arm 105 moves in response to being driven by motor 103 and primary spring 106. As depicted in FIGS. 1-7, selectively adjusting the flex of secondary spring 107 with fine adjustment device 108 controls how second arm 105 moves in response to first arm 104 and primary spring 106 moving towards the marking area. With reference to FIGS. 1-7, secondary spring 107 and fine adjustment device 108 controls the degree to which first arm 104 resiliently whips second arm 105 towards the marking area when first arm 104 moves towards the marking area.

With reference to FIGS. 1-4 and 7, secondary spring 107 is coupled to first arm 104 and to second arm 105. As shown in FIGS. 1-4 and 7, secondary spring 107 is substantially planer. The reader can see in FIGS. 1-4 and 7 that secondary spring 107 overlies a portion of primary spring 106.

The size of the secondary spring may be varied as needed for a given application. In some examples, the secondary spring is larger relative to the other components than depicted in the figures. In other examples, the secondary spring is smaller relative to the other components than depicted in the figures. Further, the reader should understand that the secondary spring and the other components may all be larger or smaller than described herein while maintaining their relative proportions.

Fine Adjustment Device

With reference to FIGS. 1-7, fine adjustment device 108 is configured to selectively adjust the flex of primary spring 106 and secondary spring 107. As shown in FIGS. 1-7, fine adjustment device 108 is operatively coupled to primary spring 106 and secondary spring 107. The reader can see in FIGS. 1-7 that fine adjustment device 108 is configured to be manually operated with a finger when operating tattoo machine 100.

As depicted in FIGS. 1-7, fine adjustment device 108 includes a nut 110, a first compression screw 111, a second compression screw 112, a compression set screw 113. The reader can see in FIGS. 1-7 that nut 110 abuts secondary spring 107. Nut 110 presses on secondary spring 107 over a user selectable range of pressure to adjust the flex of secondary spring 107.

As depicted in FIGS. 1-7, first compression screw 111 selectively adjusts the compressive force exerted by nut 110 on secondary spring 107. First compression screw 111 selectively adjusting the compressive force exerted by nut 110 on secondary spring 107 serves to selectively adjust the flex of secondary spring 107.

With reference to FIGS. 1-7, second compression screw 112 is operatively coupled to first compression screw 111. With reference to FIGS. 1-7, second compression screw 112 selectively restricts first compression screw 111 from moving absent manual engagement by a user. Second compression screw 112 selectively restricting first compression screw 111 from moving maintains the user-selected compressive force exerted by nut 110 on secondary spring 107 as tattoo machine 100 operates.

As shown in FIGS. 1, 2, and 7, compression set screw 113 is mounted to second compression screw 112 and abuts first compression screw 111. Compression set screw 113 functions to restrict first compression screw 111 from moving while tattoo machine 100 operates absent manual input from a user's finger.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A tattoo machine for driving a needle towards a marking area, comprising:
    a motor;
    an input spring; where the input spring is operatively connected to the motor, and a first arm operatively connected to the motor by the input spring and is driven by the motor and input spring towards the marking area;
    a second arm spaced from the first arm and configured to couple to the needle; and
    a primary spring coupled to the second arm and to the first arm, and the primary spring biased to move the first arm and the second arm away from the marking area;
    wherein the second arm is driven towards the marking area when the first arm is driven towards the marking area by the motor; where the machine further comprises a secondary spring, wherein the secondary spring couples the second arm to the primary arm;
    and the input spring, primary spring, and secondary spring are flat.

2. The tattoo machine of claim 1, wherein the secondary spring overlies a portion of the primary spring.

3. The tattoo machine of claim 2, further comprising a fine adjustment device operatively coupled to the primary spring and the secondary spring, the fine adjustment device configured to selectively adjust the flex of the primary spring and the secondary spring.

4. The tattoo machine of claim 3, wherein the fine adjustment device is configured to be manually operated with a finger when operating the tattoo machine.

5. The tattoo machine of claim 3, wherein the fine adjustment device includes:
    a nut; a first compression screw, a second compression screw, and a compression set screw; where the first compression screw that selectively adjusts the compressive force exerted by the nut on the secondary spring to selectively adjust the flex of the secondary spring.

6. The tattoo machine of claim 5, wherein: the second compression screw is operatively coupled to the first compression screw; the second compression screw selectively restricts the first compression screw from moving absent manual engagement by a user to maintain the compressive force exerted by the nut on the secondary spring as the tattoo machine operates.

7. The tattoo machine of claim 6, wherein the fine adjustment device further includes a compression set screw mounted to the second compression screw and abutting the first compression screw.

8. The tattoo machine of claim 3, wherein selectively adjusting the flex of the secondary spring with the fine adjustment device controls how the second arm moves in response to the first arm moving towards the marking area.

9. The tattoo machine of claim 8, wherein:
    the primary spring and the secondary spring resiliently whip the second arm towards the marking area when the first arm moves towards the marking area; and
    selectively adjusting the flex of the secondary spring with the fine adjustment device controls the degree to which the first arm resiliently whips the second arm towards the marking area when the first arm moves towards the marking area.

10. The tattoo machine of claim 9, wherein adjusting the speed of the motor further controls how the how the second arm moves in response to the first arm moving towards the marking area.

11. The tattoo machine of claim 1, wherein:
    the tattoo machine further comprises an anchor member disposed proximate the first arm opposite the second arm; and
    the primary spring is coupled to the anchor member.

12. The tattoo machine of claim 11, further comprising a primary spring adjustment device coupled to the anchor member and configured to adjust the flex of the primary spring.

13. The tattoo machine of claim 12, wherein the primary spring adjustment device includes:
    a primary spring adjustment screw selectively abutting the primary spring; and
    a primary spring set screw selectively fixing the position of the primary spring adjustment screw.

14. The tattoo machine of claim 1, wherein: the motor includes an output shaft;
    and wherein the input spring is coupled to the first arm and driven by the output shaft.

15. The tattoo machine of claim 11, further comprising an input adjustment device configured to adjust the position of the input spring relative to the output shaft of the motor.

16. The tattoo machine of claim 12, wherein the input adjustment device includes:
    an input adjustment screw selectively abutting the input spring; and
    an input set screw selectively fixing the position of the input adjustment screw.

17. The tattoo machine of claim 1, wherein:
    the second arm includes a post opposite the first arm; and the needle couples to the post.

* * * * *